United States Patent

Noakes et al.

[11] Patent Number: 5,992,771
[45] Date of Patent: Nov. 30, 1999

[54] HIGH VOLTAGE GENERATOR

[75] Inventors: Timothy James Noakes, Nr Mold Clwyd; Michale Leslie Green, Clwyd; Andrew Jefferies, Nr Mold Clwyd; Maurice Joseph Prendergast, Runcorn, all of United Kingdom

[73] Assignee: The Procter & Gamble Company, Cincinnati, Ohio

[21] Appl. No.: 08/817,126

[22] PCT Filed: Sep. 19, 1995

[86] PCT No.: PCT/GB95/02216

§ 371 Date: Apr. 7, 1997

§ 102(e) Date: Apr. 7, 1997

[87] PCT Pub. No.: WO96/11062

PCT Pub. Date: Apr. 18, 1996

[30] Foreign Application Priority Data

Oct. 11, 1994 [GB] United Kingdom .................... 9420511

[51] Int. Cl.⁶ ....................................................... B05B 5/00
[52] U.S. Cl. ...................... 239/690.1; 361/227; 361/228; 361/235; 136/255; 363/61
[58] Field of Search ................................. 239/690, 690.1; 250/551; 361/226–228, 235; 136/255; 310/305, 306, 308, 309; 323/906; 307/106, 110, 117; 363/61

[56] References Cited

U.S. PATENT DOCUMENTS

| 3,599,038 | 8/1971 | Skidmore ................................ 361/228 |
| 3,608,823 | 9/1971 | Buschor ................................. 239/690 |
| 3,902,108 | 8/1975 | Sion . |
| 5,009,720 | 4/1991 | Hokuyo et al. ......................... 136/255 |
| 5,063,350 | 11/1991 | Hemming et al. . |
| 5,218,305 | 6/1993 | Lunzer . |

FOREIGN PATENT DOCUMENTS

| 0 110 069 | 6/1984 | European Pat. Off. . |
| 468736 | 1/1992 | European Pat. Off. . |
| 0 472 817 | 3/1992 | European Pat. Off. . |
| 2 157 076 | 6/1973 | France . |
| 2 599 281 | 12/1987 | France . |

*Primary Examiner*—Andres Kashnikow
*Assistant Examiner*—Steven J. Ganey
*Attorney, Agent, or Firm*—William Scott Andes

[57] ABSTRACT

A high voltage generator is provided for use in applications where current demand is low but a high voltage is required. The generator comprises an array of photosensitive elements, such as an array of photovoltaic elements produced by laser scribing or etching of a wafer of material conventionally used for solar cells, the number of elements employed and their interconnection being such that a high voltage output of at least 1 kV is obtained.

16 Claims, 4 Drawing Sheets

HIGH VOLTAGE GENERATOR

This invention relates to the generation of high voltages for use in applications where current demand is small. One such application is electrostatic spraying of material where the voltage requirement may be in excess of 1 kV whilst the current requirement may be of the order of microamps or even nanoamps.

In our prior European Patent Applications relating to electrostatic spraying of materials (eg EP-A-120633, 441501, 468735, 468736, 482814, 486198, 503766 and 607182 and PCT-A-WO94/13063), various devices are described all of which employ a high voltage generator powered by a battery supply. One form of voltage generator suitable for use in such devices is described in EP-A-163390. Voltage generators of this form are expensive to manufacture and are relatively bulky especially for use in electrostatic spraying devices required to be compact in size, eg sprayers for cosmetics and perfumes. Moreover, the battery pack required for power supply must be accommodated within the housing of the sprayer and frequent battery replacement or recharging is necessary.

The present invention seeks to provide an alternative form of high voltage generator.

According to one aspect of the invention there is provided a device for producing a spray or stream of electrically charged particles comprising means defining a location from which said spray or stream is generated and a voltage generator for producing high voltage between said location and the surroundings, the generator comprising a large array of discrete voltage producing elements interconnected to produce a high voltage.

Preferably the generator is a solid state device comprising hundreds or even thousands of individual voltage producing elements which may be serially connected so that collectively they produce a high voltage output.

One form of the invention comprises an electrostatic spraying device comprising an outlet from which material to be electrostatically sprayed can be discharged, the outlet being associated with said location and the array of elements being interconnected to produce a high voltage sufficient to effect electrostatic spraying of material from the device.

Typically the current output of the generator will be such that the power rating of the generator is 100 mW or less, more usually 50 mW or less. For example, for a paint spraying device, the voltage may be in excess of 25 kV and the current of the order of 1 microamp (power rating of 30 mW) whilst for a room fragrance sprayer the voltage may be of the order of 0.5 to 2.0 mW, typically 1.2 mW (eg 100 nA current and 12 kV voltage).

The high voltage generator conveniently comprises an array of photosensitive elements so arranged as to produce a voltage output of at least 1 kV when irradiated.

Preferably the array of photosensitive elements is so arranged as to produce a voltage output of at least 4 kV, typically at least 5 kV and more preferably upwards of 8 kV.

The generator is conveniently in the form of an electronic solid state device comprising a large array of photosensitive elements. For instance, the solid state device may comprise a photovoltaic material (eg suitably doped polycrystalline silicon such as that used in the production of solar cells and solar panels) appropriately divided into discrete sections, eg by etching and/or laser scribing techniques commonly used in the production of semiconductor devices, to form a large array of photovoltaic elements interconnected in such a way as to produce, collectively, a high voltage output of the order referred to above when irradiated.

According to a further aspect of the invention there is provided a high voltage generator in the form of an integrated solid state device comprising a large array of interconnected radiation responsive elements, such as photovoltaic elements, operable to produce a voltage output of at least 1 kV when irradiated.

A cell of photovoltaic material, such as silicon doped with boron to produce a pure lattice of p-type material, can produce a relatively low voltage output (typically of the order of 0.45 V) when illuminated depending on the light intensity and load, but independently of the surface area. Current output on the other hand is related to both light intensity and the surface area of the cell. For the kind of electrostatic spraying applications with which the present invention is primarily concerned, current demand is very low (microamps and even nanoamps) and consequently, by serially connecting a sufficiently large array of low voltage output photovoltaic elements consistent with the high voltage to be secured (eg several kV and greater), it is feasible to obtain sufficiently high voltages for electrostatic spraying applications without requiring the large surface areas usually associated with solar panels.

Typically the spraying device comprises a housing including a compartment in which the material to be sprayed can be stored or for reception of a container containing the material, the material having properties, eg resistivity, suitable for electrostatic spraying.

The spraying device may be suitable for hand held use or portable, ie suitably sized for carrying as a self-contained unit using one hand.

The generator of the present invention may be embodied in any one of the various forms of spraying devices disclosed and/or claimed in any one of EP-A-120633, 441501, 468735, 468736, 482814, 486198, 501725, 503766 and 607182, PCT-A-WO94/13063 and International Patent Application No. PCT/GB94/01829, the entire disclosures of which are incorporated herein by this reference. The generator may also be embodied in a particulate material spraying device as disclosed in our copending UK patent application 9419988.2, the entire contents of which are incorporated herein.

The generator of such devices as disclosed in the above-mentioned patent specifications will be replaced by a generator of the present invention and such spraying devices may be designed for use in a wide variety of spraying applications such as spraying of paints and related formulations, spraying of cosmetics, perfumes, deodorants and other personal care and hygiene formulations, spraying of insecticides and pesticides, and dispensing of medical and pseudo-medical formulations such as ocular, oral and nasal formulations and skin treatment agents.

In one embodiment of the invention, the voltage producing elements are constituted by light sensitive elements, such as photovoltaic elements, connected in an array which is so disposed as to be irradiated by ambient light. In such an embodiment, the array may be located on an external part of the housing of the generator or a spraying device embodying the generator so as to be exposed to the surroundings. This embodiment may for instance find utility for room fragrance spraying since the generator may be active when the array is illuminated during daylight hours (and night time when the room lighting is switched on) but is deactivated during the hours of darkness when the room lighting is switched off.

Means may be provided for selectively exposing and shielding the array to/from ambient radiation/light according to whether high voltage output is required. For instance, the housing of the generator or spraying device may be provided with a sheath or other radiation shielding device movable between positions in which it conceals or exposes the array to the surroundings. The shield may alternatively be in the form of a removable cover which, when mounted on or attached to the generator or spraying device, prevents irradiation of the array, and allows irradiation when removed, the switching action thereby being effected by removal and replacement of the cover.

The shield/cover may be adjustable to vary the extent of exposure of the array and thereby vary the rate of spraying for instance.

Where the spraying device is designed for hand-held use, eg a paint spraying gun or an applicator for personal care or hygiene formulations and the like, the device may comprise a portion intended to be held in the hand, eg a hand grip, and a section which would not normally be encompassed by the hand in use of the device the array of photosensitive elements being disposed on the latter section so as to be exposed to ambient radiation/light.

When the array is arranged on a section of the device so as to be exposed in use, the array may be protected from damage by a superimposed layer or cover of material which is at least partially transmissive to the radiation/light.

In another embodiment, the voltage producing elements are constituted by radiation sensitive elements connected in an array arranged to be irradiated by a radiation source forming part of the generator and/or the spraying device (as the case may be). The radiation source may constitute the sole or primary source of radiation for the array or it may serve to supplement ambient radiation/light. For instance, the radiation source may be a radiation emitting element such as a light emitting solid state element (eg a light emitting diode), a filament (eg light bulb) which emits light when current is passed through the filament or a fluorescent lamp. Switching on and off of the generator in this instance may be controlled by switching the radiation emitting element on and off, in which case the switching device need only be a low voltage switch controlling a high voltage output. Alternatively switching on and off of the generator may be effected by means operable to expose and shield the array selectively to/from the radiation emitting element and such means may be movable by the user between exposure and shielding positions relative to the array.

Where the generator and/or spraying device includes such a radiation source, the source may be connected to terminal means to which an electrical power source (such as a low voltage battery) is connectable. In this event, the housing of the spraying device preferably includes a compartment for insertion of the power supply and, if desired, the radiation source and the high voltage generator may be accommodated internally of the housing. Activation and deactivation of the generator may be effected by means of a user-controllable switch forming part of an electric circuit including the terminal means and the power supply (in use).

Exposure of the array (for example to control switching on and off of the generator) may be controlled by means of a user controllable actuator. In the case of a spraying device, the actuator may serve to control the supply of material to the outlet of the device and may also be coupled with a movable masking element so that, in response to delivery of the material to the spraying outlet, the array is exposed to produce high voltage for application to the material and thereby deliver a spray of electrically charged material. In a typical embodiment, the spraying device comprises a user operable trigger for applying pressure to electrostatically sprayable material contained in a reservoir or container (for example in the form of a piston and cylinder type device or in the form of a compressible container) to effect delivery of the material to the spraying outlet, and the trigger is coupled to a masking element which is moved relative to the array (translationally or rotationally) to expose or increase exposure of the array to ambient radiation or to radiation from an associated radiation source. Alternatively, the masking element may be omitted and the radiation source may be energised in response to actuation of the trigger whereby the array is irradiated in the course of operating the trigger to deliver the material to the spraying outlet.

If employed, the radiation source may serve a dual purpose, ie the production of light for irradiation of the photosensitive array, and for producing light for illumination of the object/target to be sprayed. In addition, the radiation source may also provide an indication as to whether the device is operational or not.

As disclosed in EP-A-468735 and 468736 and PCT-A-WO94/13063, it is desirable in some applications to provide a bipolar high voltage output, for example for the purposes of shock suppression and/or to allow the spraying of electrically insulating materials such as plastics, human hair etc, which are otherwise difficult to spray. The generator of devices in accordance with the present invention may, for such applications, be arranged to provide a bipolar output, eg with an output frequency as disclosed in EP-A-468735 and 468736. For example, the high voltage output of the generator may be electronically switched at a desired frequency (which may be user-controlled) by means of electrical circuitry associated with the generator to produce bipolar output, eg using high voltage switching arrangements as disclosed in PCT-A-WO94/13063. Alternatively a generator in accordance with the invention may comprise two arrays of photosensitive elements, the arrays being configured to produce respective positive and negative high voltage outputs and control means being provided to irradiate the arrays alternately (either by ambient radiation/light or by radiation/light produced by an associated radiation source or sources) so that the composite output alternates between positive and negative values at a frequency determined by the control means.

In a specific embodiment, a spraying or ionising device may comprise two high voltage generators of the solid state type disclosed above with radiation responsive switching means of the form disclosed in International Application No. WO94/13063 arranged to alternately switch the generators in such a way that a bipolar voltage is applied to the location or site from which a spray or a stream of ions is to be generated, positive voltage being derived from one generator and negative voltage from the other. For instance, each generator may be coupled to said location through a respective radiation responsive switching means and control circuitry may be provided to operate the switching means in alternating fashion with a predetermined periodicity by controlling the radiation sources associated with each switching means.

The ambit of the invention is not limited to high voltage generators for use in spraying and ionising devices. The invention may also be applied to other devices requiring a high voltage output but low current demand. In the case of an ion stream producing device such as a room ioniser, the generator may be arranged to supply high voltage to one or more terminals, eg pointed electrodes, so as to produce one or more streams of electrically charged ions. For instance, the array of voltage introducing elements may be provided on a housing intended to be located on a horizontal surfaces such as a shelf, table or the like and the array may be connected between earth, via the base of the housing, and to a terminal at which the stream of ions is produced. The terminal may be located at an apex or other pointed location on the housing and may be in the form of an small diameter electrode. In another embodiment of ioniser, the array may be connected to two terminals and arranged to produce streams of oppositely charged ions or there may be two arrays connected to respective terminals and arranged so that one terminal produces postively charged icons while the other produces negatively charged ions.

The invention will now be described by way of example with reference to the accompanying drawings, in which.

Figure 1:
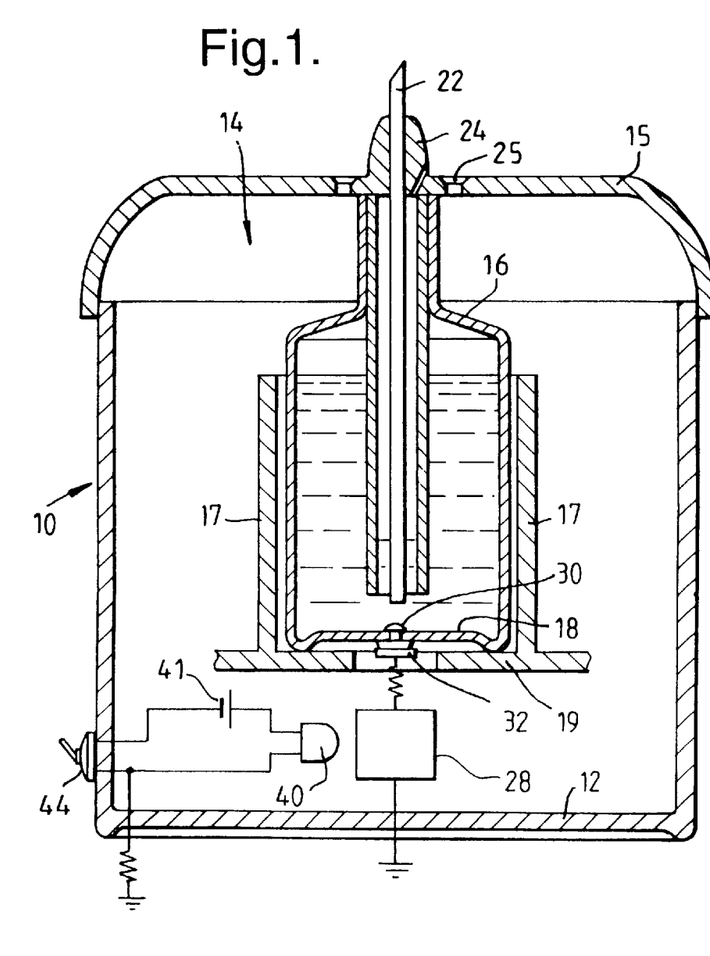
FIG. 1 is a schematic view of an electrostatic air freshener or purifiying device.

Referring to FIG. 1, the air freshener or purifying device is generally of the form described in published International Patent Application No. WO95/06521, the entire contents of which are incorporated herein by this reference. The device comprises a housing 10, the bottom wall 12 of which is intended in use to be supported on a generally horizontal surface such as a table top, a shelf or the like. The housing 10 is provided with a compartment 14 to which access can be gained by removal of cover 15 so that a cartridge 16 containing the liquid to be sprayed can be inserted into the compartment. The liquid is one suitable for electrostatic spraying and is selected to have the characteristics appropriate for the intended use of the device, ie. in this case, the liquid will have aromatic and/or air purifying properties. The cartridge 16 is received within a compartment defined by side walls 17 and bottom wall 19. A capillary structure 22 which may be in the form of a tube (but may alternatively be a wicking material such as a foam material as disclosed in International Patent Application No. WO93/06937 or a fibrous or plastics material as disclosed in EP-A-120633) is mounted within the cartridge so as to be generally vertical (ie. generally perpendicular to the horizontal bottom wall 18 of the cartridge) and its lower end is located close to the bottom wall 18 to allow liquid supply to the tube 22 to be maintained as the liquid level approaches the bottom wall 18. The upper end of the capillary tube 22 projects through a cap 24 of the cartridge and through an aperture 25 in the cover 15.

The cartridge 16 is adapted to provide for the connection of the liquid therein to the high voltage output of a high voltage generator 28. The connection may be achieved in various ways as discussed in EP-A-486198; in the illustrated embodiment, the cartridge is formed from an electrically insulating material such as nylon and is provided with an electrical contact 30. The contact 30 is located so that, when the cartridge is correctly inserted into the compartment bounded by walls 17, the contact 30 registers with a terminal 32 connected to the high voltage output of the generator 28.

The voltage generator 28 is a solid state device comprising a large array of discrete voltage producing elements, eg photovoltaic elements, which are serially connected to produce a high voltage output in response to irradiation by light or other electromagnetic radiation such as infra-red. Irradiation is provided by a radiation producing device such as a light emitting diode (LED) 40 forming part of a low voltage circuit including user operable switch 44 and low voltage source 41, eg one or more low voltage batteries (which may be rechargeable). The low voltage circuit and the generator 28 have connections to earth through the bottom wall 12 of the housing. Closing and opening of the switch 44 is effective to energise and de-energise the LED 40 thereby controlling irradiation of the photovoltaic elements of the generator 28. Thus, closure of the switch serves to irradiate the generator and produce a low current, high voltage output, typically of the order of 4 to 15 kV, and in use this voltage is applied to the liquid contents of the cartridge 16 to effect electrostatic spraying of the liquid from the tube 22. If necessary, an optical device such as a lens may be associated with the LED 40 to ensure that the radiation emitted is uniformly distributed over the array of voltage producing elements.

The capillary tube 22 is adapted to provide sufficient capillary rise when disposed vertically to feed liquid from the cartridge to its uppermost tip irrespective of the liquid level within the cartridge. This can be achieved by suitable dimensioning of the capillary tube and selection of the material from which it is fabricated. A suitable material is a polymeric material, such as nylon, polyolefine, polyacetal, polyetheretherketone or PTFE, which is adequately wetted by the formulation to be sprayed, ie the angle of contact should be substantially zero. The tube 22 in general will have a narrow bore, which may be of round section or otherwise, and a relatively thin wall. In use, the liquid is fed solely by the capillary action of the tube to the uppermost tip of the tube where it is drawn into ligaments by the high voltage applied to the liquid which issue from the tip of the tube and break up into electrically charged droplets, the droplets being drawn away from the tube tip towards objects a nd structure in the surroundings which are at earth potential. Typically, the device will be used in a room and the walls, ceiling and floor will therefore provide relatively remote targets towards which the particles are drawn.

Although in FIG. 1, the high voltage is conducted to the upper open end of the tube 22 through the liquid, in an alternative arrangement, it may be applied to the liquid at or adjacent the upper end of the tube 22 via a separate electrical lead or conductive track rather than via the body of liquid in the cartridge 16 and extending up the tube 22.

Figure 2:
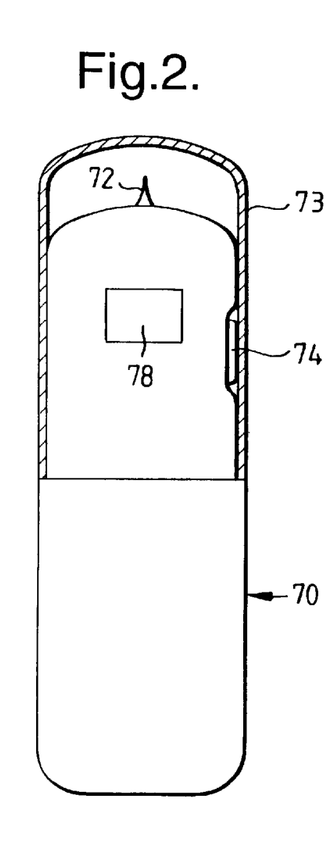
FIG. 2 is a schematic view of a self-contained hand-held spraying device for use in, for example, spraying personal care and hygiene products such as perfumes, deodorants etc.

Referring to FIG. 2, the device shown comprises a main unit 70 suitably dimensioned for holding in the hand. The unit 70 comprises a nozzle 72 to which material to be sprayed is supplied for example by passive feed where the nozzle is in the form of wicking material as disclosed for instance in EP-A-120633 or EP-A-607182 from a supply of liquid accommodated within the main unit. The unit 70 is provided with a removable cap 73. High voltage, eg 8 kV or more is applied to the liquid in operation in response to depression of a pushbutton 74 thereby causing the liquid to be delivered as a spray in the manner disclosed in EP-A-120633 or EP-A-607182. The high voltage is generated by a solid state high voltage generator comprising an array 78 of discrete voltage producing elements, such as photovoltaic elements, the array being mounted on a surface of the unit 70 which is shielded from ambient light until the cap 73 is removed. Removal of the cap 73 serves to expose the array 78 to ambient light thereby generating, without the need for a power supply, high voltage for application to the liquid as it emerges at or prior to emerging at the tip of the nozzle. The spraying operation may be initiated by depression of the pushbutton which serves to complete a circuit allowing application of the high voltage to the liquid. Alternatively, it is conceivable that the pushbutton switch could be eliminated altogether, in which event spraying may be initiated directly as a result of removing the cap to expose the array 78. Spraying can then be terminated by replacing the cap 73 to conceal the array 78 from ambient light.

In a modification, instead of requiring removal of the cap 73 to irradiate the array 78, the cap may be rotatably mounted on the unit 70 and may be provided with an opening or window which, on appropriate rotation of the cap, is brought into registry with the array 78 thereby exposing the array to light. In such a modification, the switch 74 (if needed) may be provided at a different location so as to be accessible.

Figure 3:
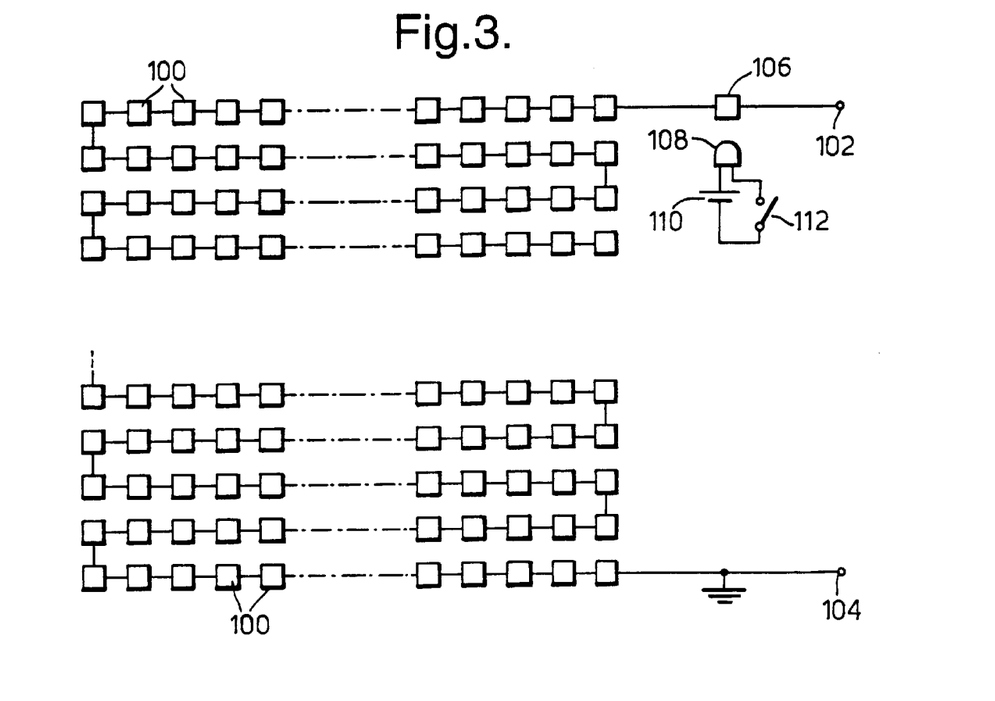
FIG. 3 is a schematic view showing a voltage generator comprising an array of voltage producing devices connected in series.

Referring to FIG. 3 one form of voltage generator suitable for use in the embodiments of FIGS. 1 and 2 comprises a large array of voltage producing elements 100, eg photovoltaic elements, on a substrate (not illustrated). The elements 100 can be produced as an integrated very large scale array by conventional techniques used in the production of electronic microchips. They are distributed in columns and rows and are connected in series as shown so that, collectively, they produce a high voltage output across terminals 102, 104. In this embodiment, a switching element 106 controls the high voltage output. The switching element may for example comprise a high voltage light sensitive diode as described in International Patent Application No. WO 94/13063. In this event, the switching element 106 may be controlled by energisation/de-energisation of a radiation source such as a light emitting diode 108 encapsulated with the high voltage diode 106 in the manner disclosed in International Patent Application No. WO 94/13063. The radiator source forms part of a low voltage circuit including battery 110 and user-actuable switch 112.

Thus, for example where the voltage producing elements 100 comprise photovoltaic cells arranged to be exposed to ambient light, if necessary the switching diode 106 may be screened from ambient light (or other source of light used to irradiate the array) so that the diode 106 is only affected by radiation emitted by the source 108. The array may be continuously exposed to ambient light or a cover or other shielding arrangement may be provided so that the array is only exposed on removal or displacement of the cover or shield. In either event, the high voltage is only applied to the terminal when switching element 106 is rendered conducting by operation of the user-operable switch 112. In a modification, the high voltage switching element 106 may be constituted by another form of electronic switching device such as a field effect transistor. Although the switching element 106 is shown connected between the array and the high voltage output terminal 102, it may instead be connected between the array and the low voltage terminal 104. Also, whilst one switching element is shown, there may be more than one arranged in series and arranged to be rendered conductive substantially simultaneously, eg. by radiation from a common light source.

Figure 4:
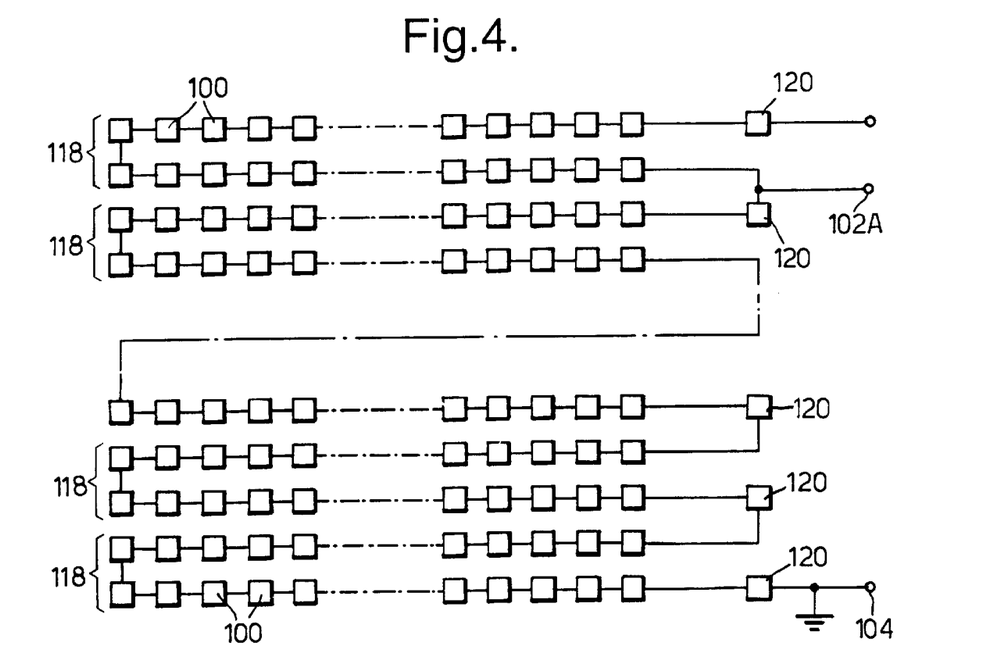
FIG. 4 is a similar view to that of FIG. 3 but showing a different switching arrangement.

FIG. 4 illustrates a modification in which the array is divided into sub-sets 118 of the voltage producing elements 100 with each sub-set having an associated switching element 120 all of which are arranged to be rendered conductive substantially simultaneously. Each sub-set 118 is series connected to the next through the switching elements 120. Thus in effect each switching element 120 serves to switch in or switch out a fraction of the total voltage. For instance, each subset 118 may comprise sufficient voltage producing elements 100 to contribute for example 100 V to the overall voltage output.

The switching elements 120 may be formed on the same substrate as the voltage producing elements 100 and may be radiation responsive, eg. in the form of photovoltaic switches rendered conductive by radiation from respective light sources (eg LEDs) or a common light source. When formed on the same substrate, suitable shielding means may be needed to shield the switching elements 120 from the light to which the voltage producing elements are exposed when for example the latter are constituted by photovoltaic cells exposed to ambient light. Alternatively, the switching elements 120 may take other forms such as field effect transistors (eg MOSFETs), the gate voltages of which may be controlled opto-electronically and/or derived by tapping voltages of suitable magnitude from the array.

In FIG. 4, the switching elements 120 when conductive serve to connect all of the sub-sets in series to produce a high voltage output at terminal 102. However, the possibility also exists of having more than one output terminal and selectively operating the switching elements so that all or only certain combinations of sub-sets are brought into operation according to the nature of the spraying operation to be carried out. The selection can be under the control of the user (e.g. by means of a suitably positioned controller on the device) where for instance the user may need to have control over the distance between the device and a target before spraying can commence. Alternatively the selection may be preset so that a common design of voltage generator can be used in devices intended for different applications requiring different output voltages. For instance, as illustrated in FIG. 4 other switching elements 120 may be connected between the array and output terminals such as 102A . . . etc. In this way, if for example the element 120 associated with the terminal 102 is not irradiated or otherwise switched into its conductive state, a lower voltage may be tapped from the array via terminal 102A etc.

Figure 5:
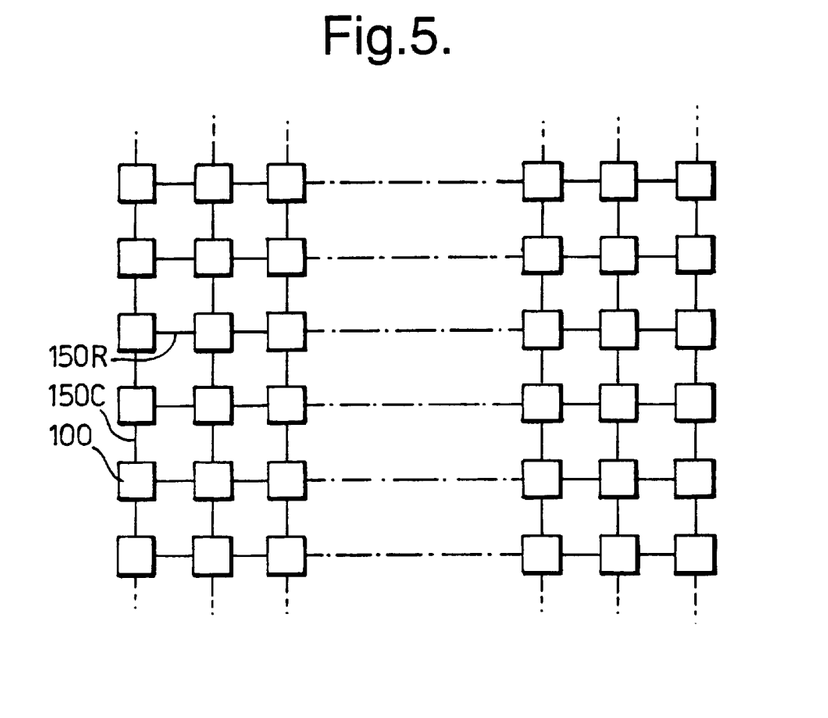
FIG. 5 is a diagrammatic view of part of an array of voltage producing elements illustrating one method of fabrication.

As indicated above, different applications will tend to require voltage generators having different output voltages. For ease and economy of manufacture, the array of voltage producing elements or cells may be initially fabricated according to a common design and then customised according to the output voltage and current characteristics required. Thus for example, as shown in FIG. 5, the array is initially fabricated on a substrate with m rows and n columns of voltage producing elements 100 with conductive tracks 150R and 150C linking each element with its immediate row-wise and column-wise neighbours. In FIG. 5, the elements at the right and left hand sides form the end columns of the array. Before the array of FIG. 5 can be used, it then has to be suitably configured by eliminating certain of the conductive tracks 150R and/or 150C. Removal can be effected by any suitable technique such as etching and may be effected in one step by use of a mask protecting those conductive tracks which are to be left intact. The array will also be provided with output terminals such as terminals 102, 104 shown in FIG. 3 either during initial fabrication or subsequently.

Figure 6:
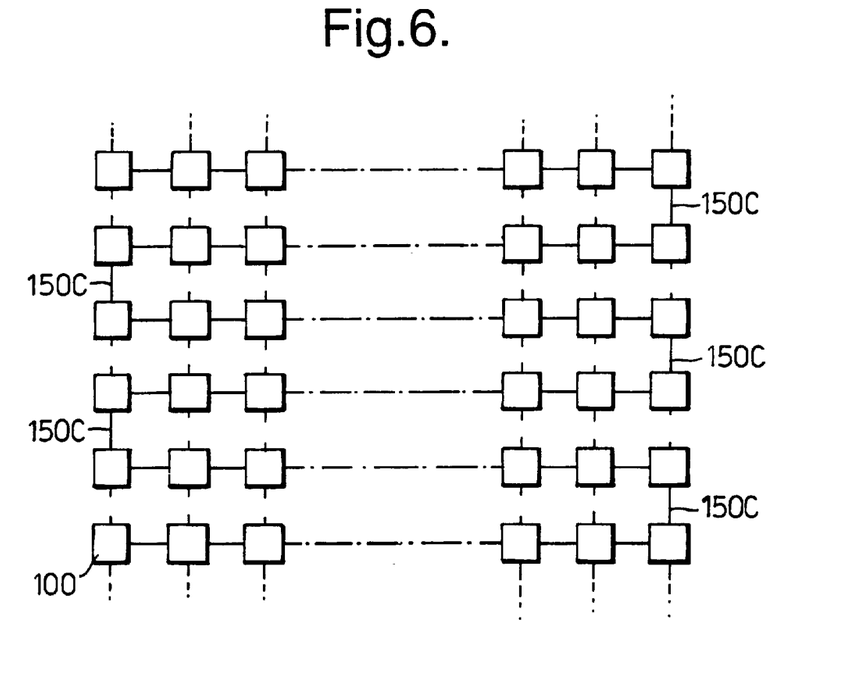
FIG. 6 is a view similar to that of FIG. 5 showing one configuration of the array in which the voltage output of the array is maximised.

FIG. 6 shows one configuration which corresponds to that of FIGS. 3 and 4. In this case, the etching or other removal technique has been used to place all of the elements 100 in a series connection by eliminating most, but not all, of the column-wise conducting connections 150C. Only those paths 150C necessary to connect together successive rows in serial fashion are left intact. Thus, in an array which comprises m x n elements each having a voltage output capability of 0.45 Volts, the total voltage obtainable from the array in this configuration is 0.45 mn Volts.

Figure 7:
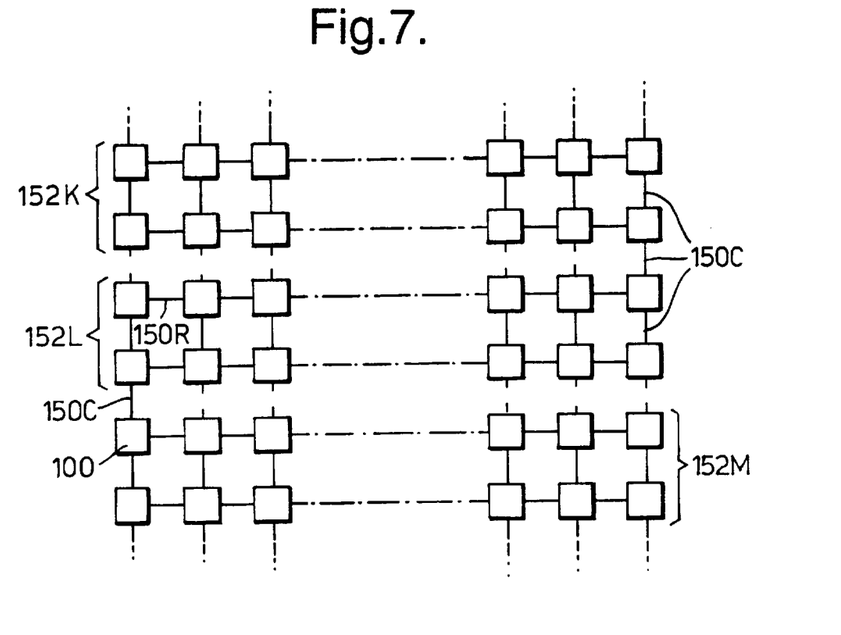
FIG. 7 is a view similar to that of FIG. 5 showing an alternative configuration of the array which produces a lower voltage output but higher current output compared with the configuration of FIG. 6.

FIG. 7 shows an alternative configuration in which at least some of the voltage producing elements are grouped in parallel with each other. Thus, as shown, successive pairs of rows may be linked by leaving appropriate ones of the column-wise conducting paths 150C intact and each pair of rows 152K, 152L, 152M . . . are connected in series with each other. In an array which comprises mxn elements each having a voltage output capability of 0.45 volts, the total voltage obtainable from the array having the configuration of FIG. 7 is 0.45 mn/2 volts, ie less than that of FIG. 6 but with a higher current output.

It will be understood that FIGS. 6 and 7 are merely examples of the various configurations that can be adopted. In some cases, for example, elimination of the conducting paths may result in some of the elements 100 being isolated from the remainder of the array so that they do not contribute to the output voltage obtained from the array. Also instead of intially fabricating the array with all of the elements 100 electrically connected with their neighbours as shown in FIG. 5, in an alternative fabrication method, the array may be initially produced with all of the elements 100 isolated from each other and the desired configuration of series or series/parallel connections may be applied subsequently by deposition or otherwise applying conductive links to the substrate at locations between those elements 100 which are to be connected in series and/or parallel.

In the embodiments described above, the voltage generator produces a unipolar output. As discussed earlier, it may be desirable in some circumstances to provide a bipolar output—e.g. for reasons of shock suppression and/or for spraying targets of an insulating nature as disclosed in EP-A-468735 and 468736.

Figure 8:
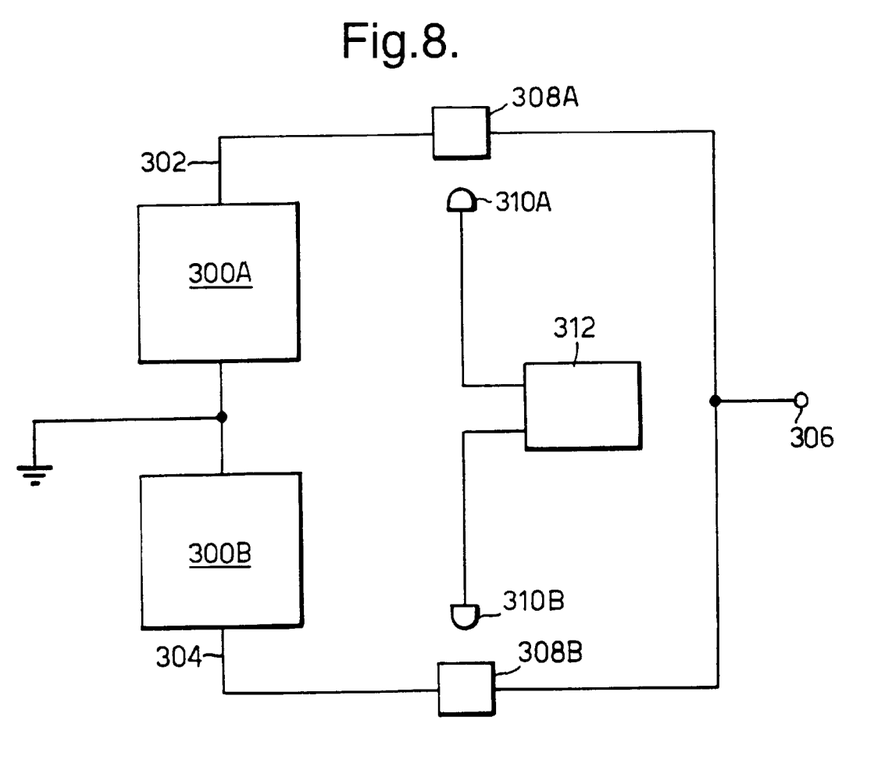
FIG. 8 is a schematic view of a bipolar form of voltage generator.

FIG. 8 illustrates one form of bipolar high voltage generator in accordance with the invention. The generator comprises two arrays 300A and 300B of voltage producing elements, such as photovoltaic cells, so arranged that array 300A produces a positive high voltage on line 302 while array 300B produces a negative high voltage on line 304. These voltages are coupled to an output terminal 306 of the generator by respective high voltage switches 308A, 308B. These switches may be of any suitable form, such as those previously described, but for the sake of illustration they are shown as being radiation responsive with each switch having an associated radiation source 310A and 310B such as a light emitting diode. Each source 310A, B is controlled by controller 312 so that they operate to open and close the switches 308A, B in alternating fashion thereby alternately coupling the positive and negative high voltage outputs of the arrays 300A, B to the output terminal 306. The frequency of the alternating voltage produced at terminal 306 is determined by the controller 312 and may be selected in accordance with the teaching in EP-A-468735 and 468736.

Although the arrays 300A and 300B are shown separately, they may be supported on a common substrate and may be sub-sets of a larger array which has been suitably configured generally in the manner described in connection with FIGS. 5 to 7.

We claim:

1. A device for producing a spray or stream of electrically charged particles comprising means defining a location from which said spray or stream is generated and a voltage generator for producing high voltage between said location and the surroundings, the generator comprising a large, solid state, array of discrete radiation sensitive voltage producing elements interconnected to produce a high voltage.

2. A device as claimed in claim 1 in the form of an electrostatic spraying device comprising an outlet from which material to be electrostatically sprayed can be discharged, the outlet being associated with said location and the array of elements being interconnected to produce a high voltage sufficient to effect electrostatic spraying of material from the device.

3. A device as claimed in claim 1 in which said elements are so interconnected as to produce a voltage output of at least 1 kV.

4. A device as claimed in claim 1 which is suitable for hand held use or suitably sized for carrying as a self-contained unit using one hand.

5. A device as claimed in claim 1 in which the generator is arranged to produce a bipolar output.

6. A device as claimed in claim 1 including two of said voltage generators and means for utilising the voltage outputs thereof in alternating fashion to produce a bipolar output.

7. A device as claimed in claim 1 in which the array is divided into a plurality of sub-sets of said voltage producing elements with each sub-set having a respective switching element associated therewith.

8. A device as claimed in claim 7 in which the switching elements are radiation responsive and means is provided for irradiating the switches to render them operable to interconnect the sub-sets.

9. A device for producing a spray or stream of electrically charged particles comprising means defining a location from which said spray or stream is generated and a voltage generator for producing high voltages between said location and the surroundings, the generator comprising a large array of discrete voltage producing elements which are radiation sensitive and are interconnected to produce a high voltage.

10. A device for producing a spray or stream of electrically charged particles comprising means defining a location from which said spray or stream is generated and a voltage generator for producing high voltage between said location and the surroundings, the generator comprising a large array of discrete voltage producing elements which are radiation sensitive and are interconnected to produce a high voltage, means being provided for selectively exposing and shielding the array to/from ambient radiation.

11. A device as claimed in claim 10 in which said means is in the form of a radiation shielding device movable between positions in which it conceals or exposes the array to the surroundings.

12. A device as claimed in claim 11 in which the shielding device comprises a removable cover which, when mounted on or attached to the device, prevents irradiation of the array, and allows irradiation when removed, the switching action thereby being effected by removal and replacement of the cover.

13. A device as claimed in claim 11 in which the shielding device is adjustable to vary the extent of exposure of the array to ambient radiation.

14. A device as claimed in claim 10 in which the array is arranged to be irradiated by a radiation source forming part of the device or generator.

15. A device as claimed in claim 10 in which exposure of the array is controlled by means of a user controllable actuator.

16. A device as claimed in claim 15 in which the actuator is operable to control the supply of material to the outlet of the device.

* * * * *

UNITED STATES PATENT AND TRADEMARK OFFICE
CERTIFICATE OF CORRECTION

PATENT NO. : 5,992,771
DATED : November 30, 1999
INVENTOR(S) : Noakes et al.

It is certified that error appears in the above-identified patent and that said Letters Patent is hereby corrected as shown below:

Title page,
Item [57], ABSTRACT,
Line 3, delete "photosensitive" and insert -- voltage producing --.

Signed and Sealed this

Second Day of December, 2003

JAMES E. ROGAN
*Director of the United States Patent and Trademark Office*